United States Patent
Yamamichi et al.

(10) Patent No.: US 8,148,140 B2
(45) Date of Patent: Apr. 3, 2012

(54) TARGET SUBSTANCE DETECTING ELEMENT, TARGET SUBSTANCE DETECTING APPARATUS, AND TARGET SUBSTANCE DETECTING METHOD

(75) Inventors: Junta Yamamichi, Cambridge, MA (US); Tetsunori Ojima, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 579 days.

(21) Appl. No.: 12/294,611

(22) PCT Filed: May 11, 2007

(86) PCT No.: PCT/JP2007/060172
§ 371 (c)(1),
(2), (4) Date: Sep. 25, 2008

(87) PCT Pub. No.: WO2007/132924
PCT Pub. Date: Nov. 22, 2007

(65) Prior Publication Data
US 2009/0104716 A1    Apr. 23, 2009

(30) Foreign Application Priority Data

May 12, 2006    (JP) .................................. 2006-133848
May 10, 2007    (JP) .................................. 2007-125241

(51) Int. Cl.
*G01N 33/553* (2006.01)
(52) U.S. Cl. ............... 435/287.2; 422/82.11; 435/288.7; 436/524; 436/525
(58) Field of Classification Search ........................ None
See application file for complete search history.

(56) References Cited

U.S. PATENT DOCUMENTS 7,008,794 B2 *   3/2006   Goh et al. ..................... 436/164
(Continued)

FOREIGN PATENT DOCUMENTS

JP             11-237337           8/1999
(Continued)

OTHER PUBLICATIONS

PCT International Search Report and Written Opinion of the International Searching Authority, Mailing Date Sep. 4, 2007.

(Continued)

*Primary Examiner* — Chris L Chin
(74) *Attorney, Agent, or Firm* — Fitzpatrick, Cella, Harper & Scinto

(57) ABSTRACT

The present invention enables to classify and measure two or more kinds of target substances which have the same recognition site recognized by a specific capturing body. Specifically, by using a target substance detecting element for detecting two or more targets, whose kinds are different mutually, at the same time, the target substance detecting element, characterized by having a base material, two or more kinds of metal structures provided on a surface of the base material, and a target capturing body provided on each surface of the two or more kinds of metal structures, and in that the number of kinds of the metal structures are equal to or more than the number of kinds of the target substances, concentrations of the two or more kinds of target substances can be calculated by integrating and analyzing detection signals detected from the target substance detecting element.

4 Claims, 18 Drawing Sheets

U.S. PATENT DOCUMENTS

| | | |
|---|---|---|
| 7,030,988 B2 | 4/2006 | Kubo et al. |
| 7,348,185 B2 | 3/2008 | Yamamichi |
| 2004/0155309 A1 | 8/2004 | Sorin et al. |
| 2007/0248987 A1 | 10/2007 | Imamura et al. |
| 2007/0248991 A1 | 10/2007 | Ojima et al. |
| 2008/0131320 A1 | 6/2008 | Yamamichi et al. |

FOREIGN PATENT DOCUMENTS

| | | |
|---|---|---|
| JP | 2002-277390 | 9/2002 |
| JP | 2003-57173 | 2/2003 |
| JP | 2003-121349 | 4/2003 |
| JP | 3452837 | 7/2003 |
| JP | 3579321 | 7/2004 |

OTHER PUBLICATIONS

U.S. Appl. No. 12/088,023, International Filing Date Dec. 20, 2006, Yamamichi, et al.

U.S. Appl. No. 10/582,805, International Filing Date Apr. 27, 2006, Yamamichi, et al.

U.S. Appl. No. 11/914,500, International Filing Date Jul. 28, 2006, Yamamichi, et al.

U.S. Appl. No. 11/913,047, International Filing Date May 29, 2006, Shiotsuka, et al.

U.S. Appl. No. 11/913,045, International Filing Date May 30, 2006, Shiotsuka, et al.

U.S. Appl. No. 12/143,604, filed Jun. 20, 2008, Nishiuma, et al.

* cited by examiner

TARGET SUBSTANCE DETECTING ELEMENT, TARGET SUBSTANCE DETECTING APPARATUS, AND TARGET SUBSTANCE DETECTING METHOD

TECHNICAL FIELD

The present invention relates to a target substance detecting element, a target substance detecting apparatus, and a target substance detecting method.

BACKGROUND ART

Japanese Patent No. 3452837 discloses a localized surface plasmon resonance sensor which detects a substance near metal microparticles using localized surface plasmon resonance induced by the metal microparticles immobilized on a base material.

In addition, Japanese Patent No. 3579321 discloses a simultaneous analysis of many components using a two-dimensional imaging surface plasmon resonance sensor.

Furthermore, Japanese Patent Application Laid-Open No. H11-237337 discloses a surface plasmon resonance method of labeling a specific component with an absorption substance using rod-shaped golden fine grains with two or more plasmon resonance wavelengths, and detecting only a specific component from a sample in which many components are intermingled.

Nevertheless, also in any sensor, it has been hard to detect separately two or more kinds of target substances which have the same recognition site recognized by a specific capturing body.

DISCLOSURE OF THE INVENTION

The present invention is directed to a target substance detecting element for detecting simultaneously target substances which have the same recognition site recognized by a specific capturing body but different in kind, comprising a base material, two or more kinds of metal structures provided on a surface of the base material, and a target capturing unit provided on each surface of the metal structures, the number of kinds of the metal structures being more than the number of kinds of the target substances.

The metal structures different in kind can be different from each other in shape or material.

The metal structures can be arranged with respect to kind.

The present invention is directed to a target substance detecting apparatus which detects kinds of target substances, comprising a target substance detecting element, a reaction mechanism for contacting a sample containing a target substance with the target substance detecting element, a light source for irradiating the target substance detecting element with light, a detecting unit for detecting a detection signal from the target substance detecting element, and an analyzing unit for analyzing the detection signal to determine the target substance, the target substance detecting element comprising a base material, two or more kinds of metal structures provided on a surface of the base material, and a target capturing unit provided on each surface of the metal structures;

the detecting unit acquiring a spectrum of outgoing light from the target substance detecting element contacted with the sample, classifying the acquired spectrum according to kind of the metal structures to determine spectral peaks, and detecting a change of the spectral peak of each kind of the metal structures from the state before the contact with the sample to the state after the contact as the detection signal; and the analyzing unit integrating and analyzing the detected detection signals to calculate the concentration of each kind of the target substances.

The number of kinds of the metal structures can be equal to or more than the number of kinds of the target substances.

The analyzing unit can use simultaneous equations with several unknowns to calculate the concentration.

The detecting unit can use a localized surface plasmon resonance method to perform the detection.

The analyzing unit can calculate the concentration from data for a calibration which has been obtained beforehand through solutions of the target substance in known concentrations.

The present invention is directed to a target substance detecting method for detecting simultaneously target substances different in kind, comprising the steps of:

contacting a sample including the target substances with a target substance detecting element comprising a base material, two or more kinds of metal structures provided on a surface of the base material, and a target capturing unit provided on each surface of the metal structures;

irradiating the target substance detecting element with light;

acquiring a spectrum of outgoing light from the target substance detecting element;

classifying the acquired spectrum according to kind of the metal structures to determine spectral peaks, to detect a change of the spectral peak of each kind of the metal structures from the state before the contact with the sample to the state after the contact as a detection signal; and integrating and analyzing the detected detection signals to calculate the concentration of each kind of the target substances.

The number of kinds of the metal structures can be equal to or more than the number of kinds of the target substances.

The detecting step can use a localized surface plasmon resonance method to perform the detection.

The calculation of the concentration in the analyzing step can be carried out from data for a calibration which has been obtained beforehand through solutions of the target substance in known concentrations.

The analyzing step can use simultaneous equations with several unknowns to calculate the concentration.

The present invention is directed to a target substance detecting method for detecting simultaneously target substances which have the same recognition site recognized by a specific capturing body but different in kind, comprising the steps of:

contacting a sample including the target substances with a target substance detecting element comprising a base material, two or more kinds of metal structures having a plurality of optical resonance modes and provided on a surface of the base material, and a target capturing unit provided on each surface of the metal structures;

irradiating the target substance detecting element with incident light;

acquiring a spectrum of outgoing light from the target substance detecting element;

determining spectral peaks corresponding to a specific resonance mode in the optical resonance modes from the acquired spectrum to detect changes of the spectral peaks from the state before the contact with the sample to the state after the contact as a detection signal at every spectral peaks; and analyzing the detected detection signals to calculate the concentration of each kind of the target substances.

In view of the above-mentioned issues, the present invention aims at classifying and measuring two or more kinds of target substances which have the same recognition site recognized by a specific capturing body.

In addition, the another present invention is a target substance detecting element, characterized by having a base material, two or more kinds of metal structures provided on a surface of the base material, and a target substance capturing body provided on each surface of the two or more kinds of metal structures.

The above-described target substance detecting element is a target substance detecting element for detecting two or more target substances, which have the same recognition site recognized by a specific capturing body but whose kinds are different mutually, at the same time, and the number of kinds of the above-described metal structures can be more than the number of kinds of the above-described target substances.

What are mutually different in kind among the above-described metal structures can be mutually different in shape or material.

The two or more kinds of above-mentioned metal structures are arranged independently for every metal structure belonging to the same kind.

In addition, the still another present invention is a target substance detecting apparatus which detects two or more kinds of target substances and has:

at least a target substance detecting element;

a holding unit for holding the target substance detecting element;

a detecting unit for detecting a detection signal obtained from the above-described target substance detecting element; and an analyzing unit for analyzing the above-described detection signal and performing a quantitative analysis of the above-described target substance, the target substance detecting apparatus being characterized in that the above-described target substance detecting element is a target substance detecting element which has a base material, two or more kinds of metal structures provided on a surface of the base material, and the above-described target substance capturing body provided on each surface of the two or more kinds of metal structures;

that the above-described detecting unit is a detecting unit which can classify and detect a detection signal for every kind of the above-described metal structures which the above-described target substance detecting element has; and that the above-described analyzing unit is an analyzing unit which integrates and analyzes detection signals classified and detected for every kind of the above-described metal structures, and calculates concentrations of the above-described target substances for every kind of the above-described target substances.

The number of kinds of the above-described metal structures can be more than the number of kinds of the above-described target substances.

The above-described analyzing unit can be an analyzing unit which calculates concentrations of the above-described target substances according to calibration data which has been found beforehand with a solution which contains the above-described target substances whose concentrations are known.

The above-described analyzing unit can be an analyzing unit which calculates concentrations of the above-described target substances using simultaneous equations with several unknowns.

In addition, the another present invention is a target substance detecting method for detecting two or more target substances, which have the same recognition site recognized by a specific capturing body but whose kinds are different mutually, at the same time, the target substance detecting method being characterized by including:

contacting a sample, including the above-described two or more target substances whose kinds are different mutually, with a target substance detecting element having a base material, two or more kinds of metal structures provided on a surface of the base material, and a target substance capturing body provided on each surface of the two or more kinds of metal structures;

radiating light on the above-described target substance detecting element;

classifying and detecting a detection signal, which is obtained from the above-described target substance detecting element, for every kind of the above-described metal structures which the above-described target substance detecting element has; and performing an analysis by integrating and analyzing detection signals classified and detected for every kind of the above-described metal structures, and calculating concentrations of the above-described target substances for every kind of the above-described target substances.

The number of kinds of the above-described metal structures can be equal to or more than the number of kinds of the above-described target substances.

The above-described detecting step can be a detecting step of performing detection using a localized surface plasmon resonance method.

The above-described analyzing step can be a step of calculating concentrations of the above-described target substances according to calibration data which has been found beforehand with a solution which contains the above-described target substances whose concentrations are known.

The above-described analyzing step can be a step of calculating concentrations of the above-described target substances using simultaneous equations with several unknowns.

Further features of the present invention will become apparent from the following description of exemplary embodiments with reference to the attached drawings.

BEST MODE FOR CARRYING OUT THE INVENTION

Hereafter, although examples are cited and described about embodiments of the present invention, a target substance detecting element and a target substance detecting apparatus of the present invention are not limited to these.

First Embodiment (Target Substance Detecting Element)

Figure 7:
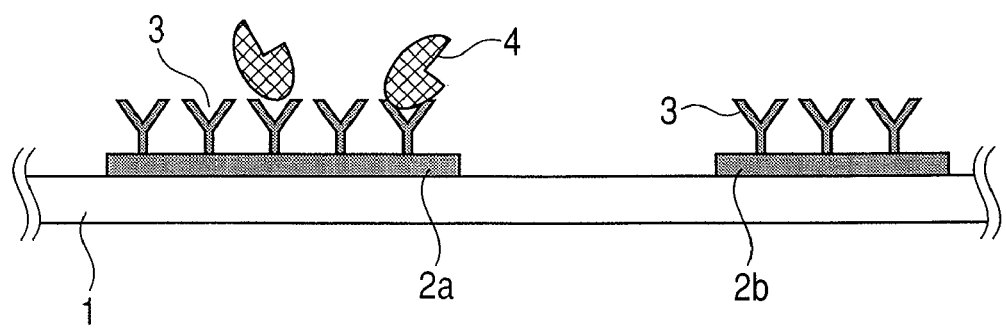
FIG. 7 is a schematic diagram illustrating an example of a target substance detecting element in a first embodiment.

FIG. 7 illustrates a conceptual diagram of a detecting element in the first embodiment of the present invention.

The detecting element of this embodiment includes a base material 1, two or more kinds of metal structures 2 immobilized to the above-described base material 1, and a target substance capturing body 3 immobilized in the above-described metal structures. In addition, two metal structures illustrated in FIG. 7 are mutually different in kind, and a size of a metal structure 2a which exists in a left-hand side is larger than a size of a metal structure 2b which exists in a right-hand side. In addition, in the present invention and this specification, the "metal structures which are different in kind" mean metal structures which are mutually different in shape, material, or the like. Furthermore, difference in shape, material, or the like between the metal structures which are mutually different in kind becomes difference between localized surface plasmon resonance states of respective metal structures. Here, suppose that "to be different in shape" includes not only a case that two-dimensional or three-dimensional shapes are different, but also a case that shapes are the same but sizes are different, that is, a case of similar figures.

When the kinds of the metal structures are different, sizes of regions (detectable regions) where electromagnetic waves, that is, localized surface plasmon near surfaces of the metal structures can exist are different. This respect will be described using conceptual diagrams in FIGS. 8A and 8B.

Figure 8A:
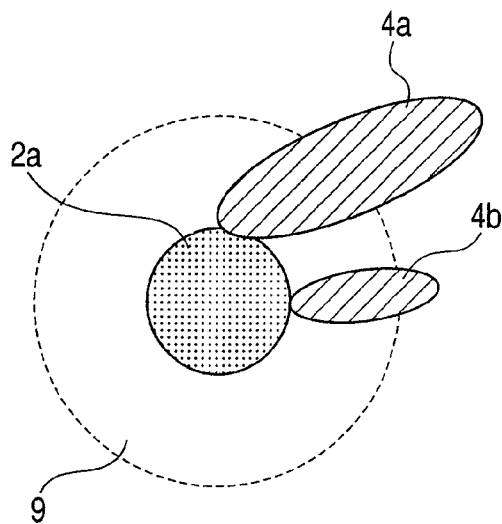
FIGS. 8A and 8B are schematic diagrams illustrating concept of a target substance detecting method in the first embodiment.
Figure 8B:
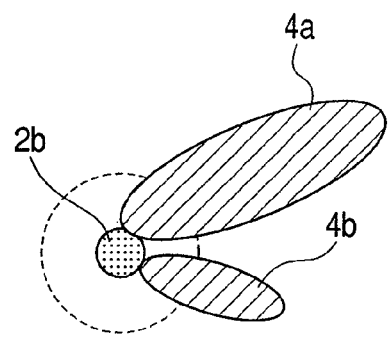

In FIGS. 8A and 8B, reference characters 2a and 2b are metal structures respectively, and they are mutually different in kind similarly to those in FIG. 7.

In FIGS. 8A and 8B, reference characters 2a and 2b are metal structures respectively, and they are mutually different in kind. In addition, in the present invention and this specification, the "metal structures which are different in kind" mean metal structures which are mutually different in shape, material, or the like. Furthermore, difference in shape, material, or the like between the metal structures which are mutually different in kind becomes difference between localized surface plasmon resonance states of respective metal structures. Here, suppose that "to be different in shape" contains not only a case that two-dimensional or three-dimensional shapes are different, but also a case that shapes are the same but sizes are different, that is, a case of similar figures.

Reference characters 2a and 2b illustrated in FIGS. 8A and 8B denote the case of similar figures conceptually. What dotted lines illustrate in FIGS. 8A and 8B are outer peripheries of regions (detectable region) where localized surface plasmon may exist. In examples illustrated in these conceptual diagrams, in this way, sizes of the detectable regions 9 are different by shapes of the metal structures being different.

In a state that the same target capturing bodies (not shown) which can capture a plurality of target substances are arranged on respective surfaces of these metal structures, target substances 4a and 4b which are mutually different in size are made to be captured by these capturing bodies. In addition, the target substances 4a and 4b are all captured by the above-described capturing bodies.

When the target substances 4a and 4b are made to be captured as illustrated in FIGS. 8A and 8B, variations of localized surface plasmon resonance of respective metal structures are different. That is, in the element conceptually illustrated in FIG. 8A and the element conceptually illustrated in 8B, a signal of one in FIG. 8A is larger, and a signal of another in FIG. 8B is smaller. In consequence, detection sensitivities are different. In addition, difference in the detection sensitivities of these elements is different between a case that only the target substance 4a is made to be captured, and a case that only the target substance 4b is made to be captured. By using this respect, simultaneous equations with several unknowns (in this example, two unknowns) which are mentioned later can be created. Respective amounts or concentrations of the target substances 4a and 4b can be found by solving these simultaneous equations.

Figure 4A:
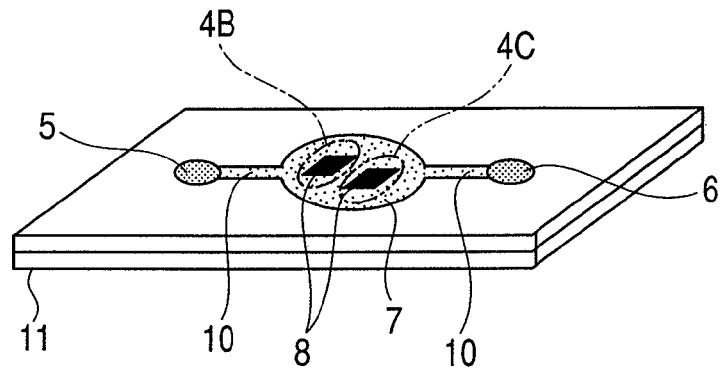
FIGS. 4A, 4B and 4C are schematic diagrams illustrating examples of a first target substance detection substrate.
Figure 4B:
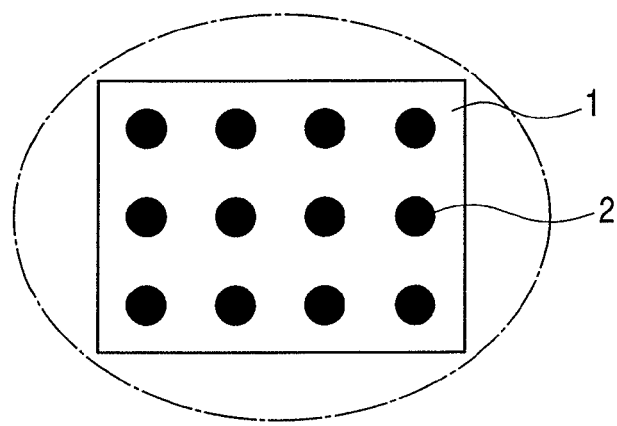
Figure 4C:
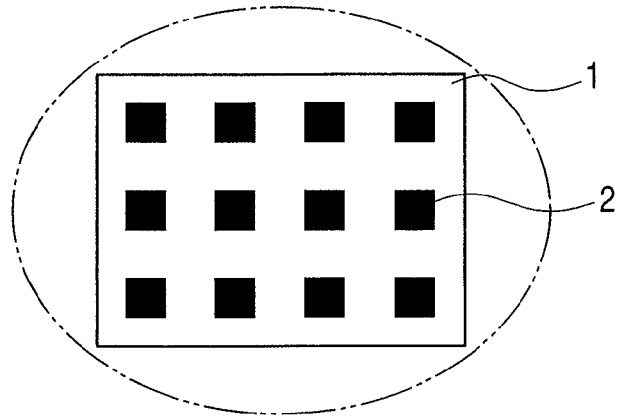

When specifically describing this a little, a plurality of detecting elements which are different in detectable region, that is, detection sensitivity can be obtained by producing two or more kinds of metal structures 2 on the base material 1 as FIGS. 4A, 4B and 4C. Two or more kinds of target substances which have the same recognition site can be classified and their quantity can be determined by forming elements which are different in detection sensitivity. In addition, when selecting a metal structure, it is necessary to select the metal structure which has a detectable region suitable for a size of a target substance which is an object.

Any metal structure may be used and there is no restriction in shape so long as it is a metal structure which can generate a localized surface plasmon resonance phenomenon. As shapes of such a metal structure, a fine grain shape, a ring shape, and a cube shape can be cited, for example.

Figure 1A:
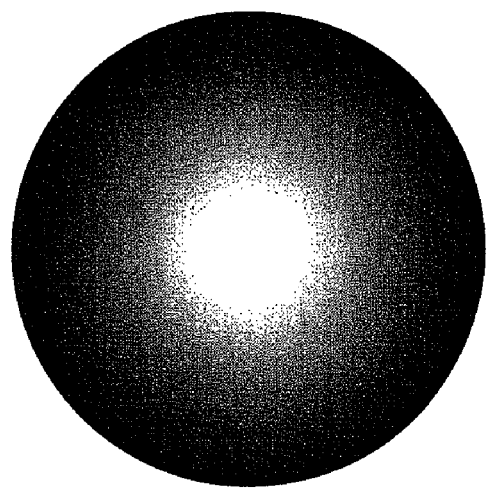
FIGS. 1A and 1B are schematic diagrams illustrating fine grain shapes of a metal structure.
Figure 1B:
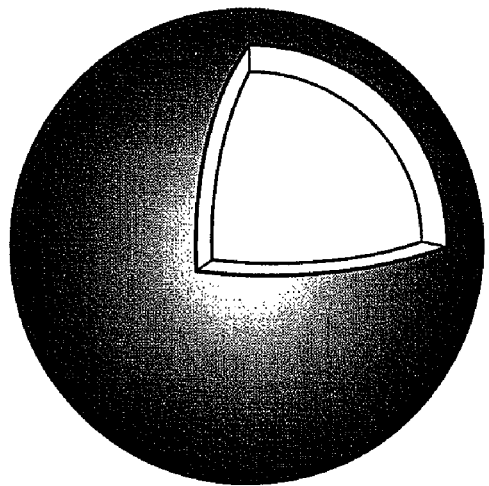

FIGS. 1A and 1B illustrate examples of a fine grain-shaped metal structure. A fine grain shape may be a fine grain formed of one kind of metal material or an alloy as shown in FIG. 1A. It may be a fine grain with core shell structure that metal colloid or a dielectric is used as a core and the above-described core is coated with a metal material as shown in FIG. 1B.

FIGS. 2C, 2D, 2E and 2F illustrate examples of a metal structure which has a shape of a round pillar or polygonal pillar.

Figure 2C:
FIGS. 2C, 2D, 2E, 2F, 2G, 2H, 2I, 2J and 2K are schematic diagrams illustrating various types of planar shapes of a metal structure.
Figure 2D:
Figure 2E:
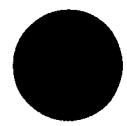
Figure 2F:
Figure 2G:
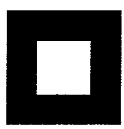
Figure 2H:
Figure 2I:
Figure 2J:
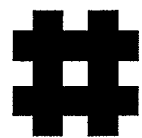
Figure 2K:
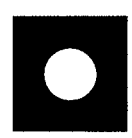

In addition, FIGS. 2G, 2H, 2I, 2J and 2K illustrate examples of a shape of a metal structure which has a loop portion. Among those, FIG. 2J is an example of a shape which has a loop portion in a part of a metal structure, and FIG. 2K is an example that an inner shape of ring and an outer shape are different. In addition, a metal structure, having two or more loop portions, and the like may be used besides these.

Figure 3L:
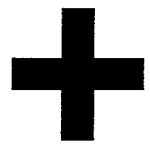
FIGS. 3L, 3M, 3N, 3O and 3P are schematic diagrams illustrating various types of planar shapes of a metal structure.
Figure 3M:
Figure 3N:
Figure 3O:
Figure 3P:
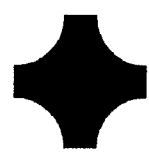

In addition, FIGS. 3L, 3M, 3N, 3O and 3P illustrate examples of a shape having a branch portion. Among those, FIG. 3L illustrates an example of a shape formed by two belt-like line segments intersecting and passing through. FIGS. 3M, 3N and 3O are examples of a shape that at least one of belt-like portions is sealed in a crossing section of line segments not to pass through to another side, and a shape that angles of a crossing section are roundly obtuse without being formed in an acute angle, as illustrated in FIG. 3P. In addition, a crossed angle of a belt-like portion is not limited to a right angle. Furthermore, in examples illustrated in FIGS. 3L, 3M, 3N, 3O and 3P, although belt-like portions are extended linearly, the belt-like portions may be extended curvedly.

Any material can be used as a material which forms a metal structure so long as it is a material which generates a localized surface plasmon resonance phenomenon. As such a material, for example, any metal of gold, silver, copper, platinum and aluminum, or an alloy of them is cited.

In addition, as a size of a metal structure, when the metal structure is a fine grain, it is preferable that it has size of 10 nm to 500 nm in diameter. In addition, when a metal structure has a shape other than a fine grain, such as a ring shape and a cube shape, suitable size of the metal structure is 10 nm to 1450 nm, and more preferably, it is 50 nm to 450 nm. In addition, preferable thickness of a metal structure is 10 nm to 100 nm. Localized surface plasmon resonance which can achieve target detection sensitivity which is an object can be generated effectively by making the size of a metal structure within these limits.

Figure 16A:
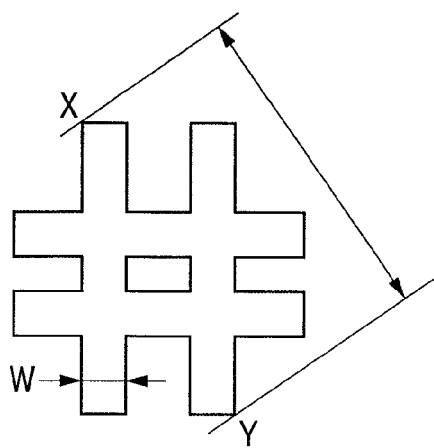
FIGS. 16A and 16B are drawings illustrating measuring methods of measuring sizes of a metal structure.
Figure 16B:
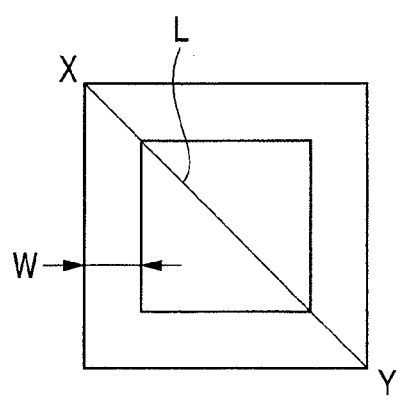

Furthermore, it is defined that size of a metal structure is a maximum of a distance between arbitrary two points in the metal structure on a plane parallel to a metal structure formed-surface of a base material. For example, in the case of a parallel crosses shape illustrated in FIG. 16A, a maximum distance is a distance between a point X and a point Y. In addition, in the case of a rectangular ring shape as shown in FIG. 16B, since a distance of a diagonal line L between X and Y on an outer peripheral shape is maximum, let L be the size of a metal structure, and in a circular ring shape illustrated in FIG. 2I, let a diameter of an outer peripheral circle be the size of a metal structure.

Moreover, metal structures illustrated in FIGS. 2G, 2H, 2I, 2J, 2K, 3L, 3M, 3N, 3O and 3P are constructed on the basis of belt-like portions. Although width of a belt-like portion is not limited in particular so long as formation of a metal structure is possible and localized plasmon resonance which is an object of the present invention can be obtained, it is preferable that it is within a range of 10 to 100 nm. Detection in high sensitivity can be achieved by making the width of the belt-like portion of a metal structure within the range of 10 nm to 100 nm. For example, in the case of a circular ring shape in FIG. 2I, the width of this belt-like portion is difference between radii of an outer circumferential circle and an inner circumferential circle, and in the case of shapes illustrated in FIGS. 16A and 16B, it is shown by portions illustrated by W. In addition, the width of the belt-like portion may be the same or may be changed in portions in the same metal structure.

The number of kinds of metal structures formed on a base material is made to be equal to or more than the number of kinds of targets. So long as the number of kinds of metal structures on the base material is equal to or more than the number of kinds of targets, one per one kind of metal structure may be provided on the base material, or two or more may be provided. In addition, two or more kinds of metal structures can be arranged independently for every metal structure belonging to the same kind. Performing such arrangement enables enhancement in manufacturing efficiency of a metal structure, facilitation of construction of a detection system, and easy acquisition of signal detection from respective elements.

In addition, in the case of being arranged independently, two or more kinds of metal structures may be provided on the same base material, or each kind of metal structure may be provided with a base material being classified. In addition, "to be arranged independently" means that each metal structure belonging to the same kind is arranged to a specific region, and those regions can be clearly distinguished. For example, as illustrated in FIGS. 4A, 4B and 4C, two or more metal structures belonging to the same kind are regularly provided in a region of about 1 mm to 10 mm square to be made an array. In the case of making them in a shape of the array, preferable intervals of metal structures are made to be 50 nm to 2 μm, and more preferably, it is made within a range of 150 nm to 1 μm. When an interval is too narrow, localized surface plasmons which respective metal structures have perform an interaction to affect distribution and strength of a spatial electric field. In consequence, sensor sensitivity may drop. In addition, since signal strength becomes weak because of low density of metal structures when an interval is too large, a special optical system becomes necessary.

Furthermore, in the remaining specification, it is made that it is expressed as two or more kinds of detecting elements also when two or more kinds of metal structures which have a capturing body on a surface are formed on the same base material.

Next, a production method of a base material which has a metal structure on a surface will be described.

FIGS. 5A, 5B, 5C, 5D, 5E and 5F illustrate an example of its production method.

Figure 5A:
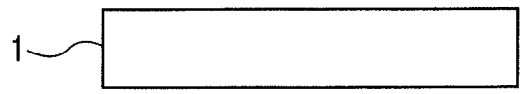
FIGS. 5A, 5B, 5C, 5D, 5E and 5F are diagrams illustrating a method of producing a part of a target substance detecting element.
Figure 5B:
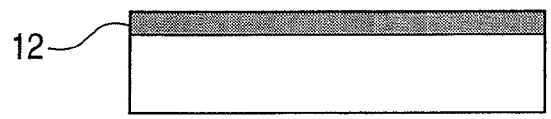
Figure 5C:
Figure 5D:
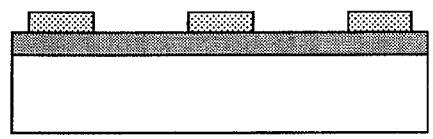
Figure 5E:
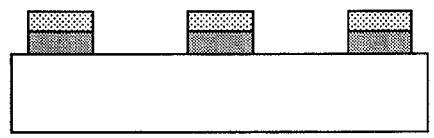
Figure 5F:
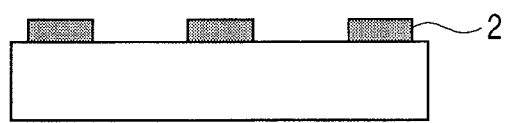

As illustrated in FIGS. 5A, 5B, 5C, 5D, 5E and 5F, a metal film 12 is formed on a base material 1 by a sputtering method or vacuum deposition (FIG. 5B). Then, an electron beam resist film 13 is formed on the above-described metal film 12 by a method such as spin coating (FIG. 5C). Only the portions, where a metal structure is formed, in the above-described electron beam resist film 13 are exposed and developed with an electron beam lithography system, and a resist pattern is obtained (FIG. 5D). Then, an unnecessary metal film is etched (FIG. 5E), the resist is removed, and metal structures 2 which are arranged in an array are obtained (FIG. 5F). Here, as an apparatus which exposes a resist, a focused ion beam processing apparatus, an X ray lithography, an EUV lithography, an excimer laser lithography, or the like can be also used besides an electron beam lithography system.

Figure 6A:
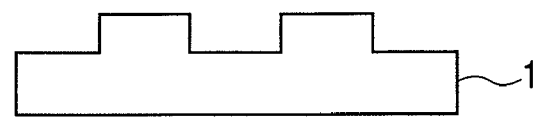
FIGS. 6A, 6B and 6C are diagrams illustrating a method of producing a part of a target substance detecting element.
Figure 6B:
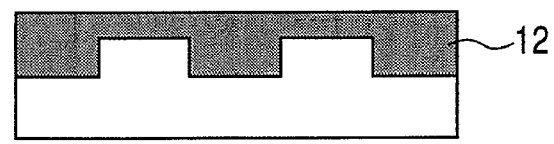
Figure 6C:
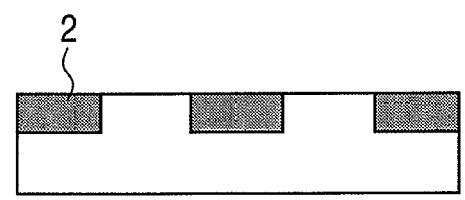

In addition, as illustrated in FIGS. 6A, 6B and 6C, the metal structures 2 can be also produced using a fine convexoconcave substrate (FIG. 6A) produced by a mold method. In this case, the metal film 12 is formed on the base material 1 by the sputtering method, vacuum deposition, or the like (FIG. 6B). Next, the metal structures 2 formed on the base material is obtained by performing grinding so that the metal film 12 may remain only in concave portions of a base material (FIG. 6C). In addition, when the metal film 12 is thinner than convexoconcave thickness of the base material 1, it becomes in the state in FIG. 6C without passing through the state in FIG. 6B, and metal structures can be obtained. In this case, height of convex portions of the base material 1 may be higher than height of the metal structures 2. In addition, the metal structures 2 may be formed as films on wall surfaces of the convexoconcave portions of the base material 1. Here, the metal film 12 can be also removed using etchback by dry etching instead of grinding.

Since the base material 1 which forms the metal structures 2 needs to be made of a material which does not absorb light, an optically transparent base material is used for it. As a material of such the base material 1, for example, glass, quartz, a resin, such as polycarbonate or polystyrene, ITO, or the like can be used. When forming the metal structures 2 on the base material 1, the metal structures may be formed after forming thin films of chromium, titanium, or the like in a base material beforehand in order to enhance adhesion between the metal structures 2 and base material 1.

A target substance capturing body immobilized on a surface of a metal structure may be anything so long as it can capture a target substance specifically.

Target substances of the present invention are two or more kinds of target substances which have the same recognition site recognized by a specific capturing body. Here, in the present invention and this specification, "target substances whose kinds are different" mean target substances which have the same property of bonding with a specific capturing body, but are not completely the same mutually. In addition, "to be not completely the same" means that target substances have difference in molecular structure, molecular weight, three-dimensional structure, and the like. Furthermore, when a plurality of target substances which do not have the same property of bonding with a specific capturing body exist in a sample, separate capturing bodies bonding with respective target substances can be respectively immobilized and used on a metal structure. As examples of such a target substance, a plurality of proteins which have the same subunit is cited. For example, lipoprotein, Alzheimer-related marker (ADDL: Amyloid β-derived diffusible ligands), a blood coagulation factor XIII, and the like have the same recognition site, but respective molecular sizes are different. Then, those sizes have important relevance to diseases. Hence, it is important to classify and detect these.

When a target substance approaches the capturing body immobilized on a metal structure, the target substance capturing body 3 and the target substance 4 form a complex specifically as illustrated in FIG. 7 to change a dielectric constant (refractive index) of a surface of the metal structure 2. As combination of such a target substance and a capturing body, for example, antigen-antibody, enzyme-substrate, sugar chain-protein, lipid-protein, RNA-protein, DNA-DNA, and the like are cited. That is, among these combinations, one side can be made into a target substance, and another side can be used as a target substance capturing body. These trapping bodies are fixed on a surface of a detecting element by a physical or chemical method. As immobilization by a physical method, for example, a method of performing immobilization by causing the capturing body to be physically adsorbed on a metal structure surface is cited. In addition, as a method of chemical immobilization, for example, a method of performing a chemical bond between a capturing body and an active group, and immobilizing them after immobilizing molecules which have the active group which immobilizes the capturing body on a metal structure surface is cited. In addition, in the present invention and this embodiment, a chemical bond is defined to be a concept including an ionic bond, a covalent bond, a coordinate bond, a metallic bond, and a hydrogen bond.

In this embodiment, although two or more kinds of metal structures exist, target substance capturing bodies are made to be immobilized on all the metal structures by similar methods. Hence, a target substance in a sample is captured by a capturing body on a metal structure at approximately uniformly according to a concentration of the target substance in the sample.

In addition, in order to prevent one other than a target substance from being adsorbed on the surface of the metal structure nonspecifically, it is preferable to coat a blocking agent on portions other than portions on which the capturing body is immobilized on the surfaces of the metal structure. As such blocking agents, for example, skim milk, casein, bovine serum albumin, phospholipid, polyethylene glycol, dextran and those derivatives are cited.

Figure 9:
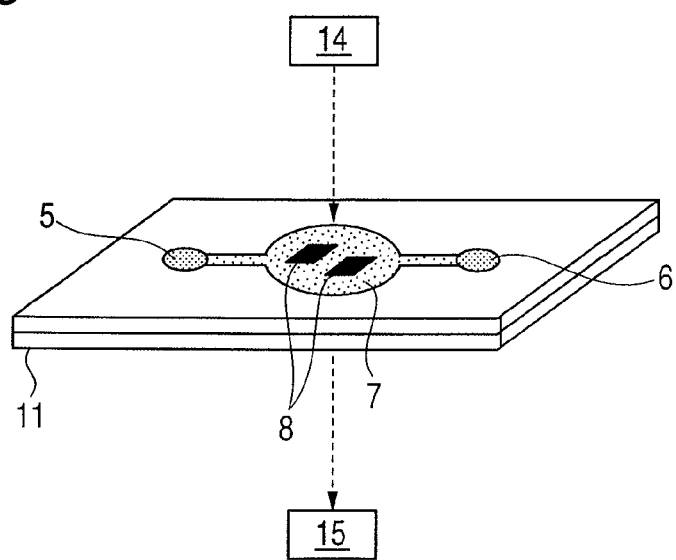
FIG. 9 is a schematic diagram illustrating an example of a target substance detecting apparatus in the first embodiment.

As illustrated in FIGS. 4A, 4B and 4C, a detecting element can be bonded to a substrate 11 which has a reaction well 7, a flow path 10, an inlet 5, and an outlet 6, and it can be used as a target substance detection substrate. Here, in the present invention and this embodiment, a detecting element is defined to be one including a capturing body which captures a target substance, a metal structure which has the above-described capturing body on a surface, and a base material which has the above-described metal structure on a surface. When bonding a detecting element and a target substance detection substrate, they can be used as a target substance detection substrate with a shape as shown in FIG. 9 by bonding together a surface of the substrate 11 in which the reaction well 7 and flow path 10 are formed, and a surface of the detecting elements 8 on which the metal structure of the base material 1 is formed. Here, the reaction well 7 means what forms a region (reaction mechanism) for contacting a detecting element and a sample.

In addition, when the base material 1 has sufficient thickness, the detecting element 8 may not be formed on the substrate 11, or the base material 1 may serve as a function (function of holding a detecting element) of the substrate 11. In that case, although it is preferable that the base material 1 has a reaction well, a flow path, an inlet, and an outlet, the flow path, inlet, and outlet may be formed of a cell or the like in contact with the base material.

As for the substrate 11 which has the reaction well 7 and flow path 10 on a surface, it is preferable that it is an optically transparent material similarly to the base material 1. Specifically, it is preferable to produce it with a plate made from a polydimethylsiloxane (PDMS) used in a so-called μTAS (Micro Total Analysis System) type device.

(Detecting Apparatus and Detecting Method)

Next, a target substance detecting apparatus and a detecting method using the above-described detecting element will be described using FIGS. 9 and 10.

First, the detecting apparatus will be described.

A target detecting apparatus according to this embodiment has at least a target substance detecting element having the above-mentioned construction, a detecting unit for detecting a detection signal obtained from the above-described target substance detecting element, and an analyzing unit for analyzing the above-described detection signal and performing a quantitative analysis of the above-described target substance.

The above-described detecting unit includes an optical system and a solution sending system. Among these, the optical system includes a light source unit 14 which includes a light source, a lens, and the like, a photo detector 15, and the like. In addition, the solution sending system includes the substrate 11 which forms a reaction region for moving a target substance to the base material which has a capturing body, and making it react, and which has the reaction well 7, inlet 5, outlet 6, and flow path 10, a solution-sending pump 16, a waste solution reservoir 17, and the like. Here, as for a forming method of the reaction well 7, inlet 5, and outlet 6, as mentioned above, it is preferable to form them by bonding the substrate which has these, and the above-described target substance detecting element.

As the light source which the light source unit 14 has, it is preferable to use what can radiates light with a wavelength from a visible region to a near-infrared region, and the photo detector 15 must be able to detect property of light, such as spectrum or strength of light emitted from the above-described light source as mention later.

A micro piston pump, a syringe pump, or the like is used as the solution-sending pump 16. In addition, it is described only when it has a solution-sending pump here, but it can be also used as what does not have a solution-sending pump, i.e., as a batch system.

In addition, the inlet 5 and outlet 6 are connected to the solution-sending pump 16 and waste solution reservoir 17, respectively.

Then, a detecting method will be described.

With using the solution-sending pump 16, a sample solution which contains a target substance is filled into the reaction well 7 through the inlet 5 and flow path 10, and with contacting the sample solution and detecting element, incubation is performed for a given length of time. When a target substance bonds with a capturing body provided on a metal structure surface of a detecting element specifically, a localized surface plasmon resonance state on the metal structure surface changes. A change of this localized surface plasmon resonance state is detected as a detection signal.

Figure 10:
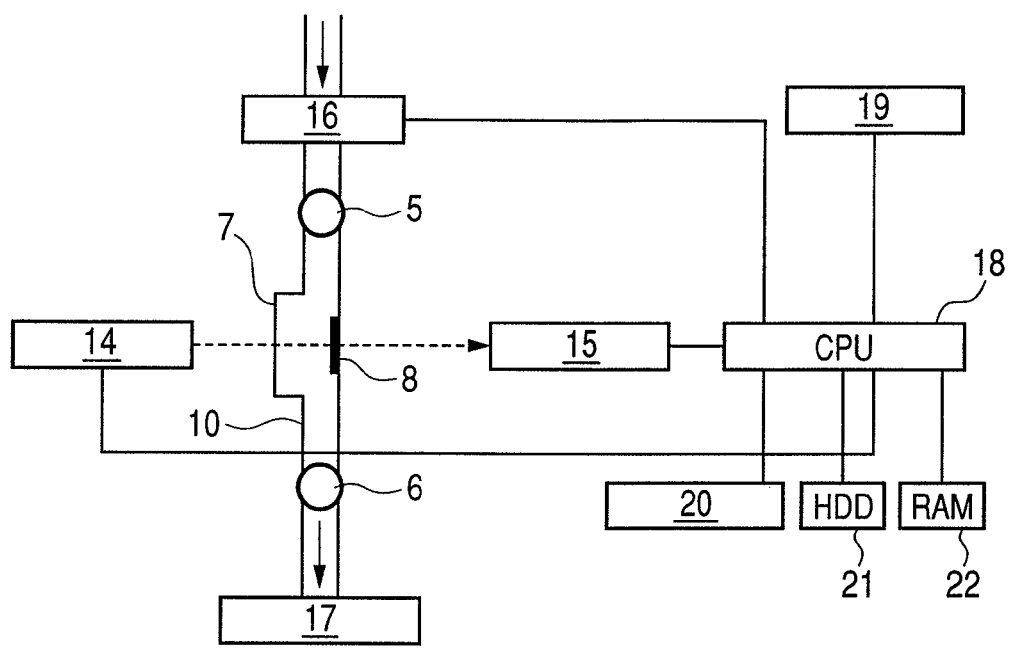
FIG. 10 is a block diagram illustrating an example of a target substance detecting apparatus in the first embodiment.

In FIG. 10, light generated from the optical unit 14 is radiated on the target substance detecting element 8, a transmission spectrum of the light after transmitting the reaction well 7 is measured with a photo detector, and a spectrum of outgoing light from the detecting element is acquired. Then, the obtained spectrum of the outgoing light is classified for every kind of metal structure, and a spectral peak is specified, and a change of the above-described spectral peak for every kind of the above-described metal structure before and after sample contact is made a detection signal. In addition, not only the transmission spectrum of light but also an absorption spectrum, a dispersion spectrum, a reflection spectrum, or the like may be sufficient as a spectrum of outgoing light. Also among them, it is preferable to use a change of a peak wavelength of an absorption spectrum or a change of absorption intensity of a peak as a signal. At this time, although a local maximum or a local minimum of a spectrum can be specified as a peak, a value near a local maximum or a local minimum on a spectrum can be also made a spectral peak. In addition, here, the value near a local maximum or a local minimum on a spectrum means a value on a spectrum in an arbitrary wavelength range near a wavelength which shows the local maximum or local minimum, and for example, it is a value on a spectrum in a wavelength range of wavelength ±5 nm, the wavelength showing the local maximum or local minimum.

In addition, when a spectrum change of light is used as a signal, although a spectroscope can be used as a photo detector, only the light at an arbitrary wavelength is taken out with a filter or the like and can be also detected with a photodiode or the like. In this case, for example, a strength change of the light before or after sample contact in a specific peak or a specific wavelength near the peak can be used as a signal. In addition, in a phase before detecting light, outgoing light is received without performing optical filtering for taking out specific light, and is filtered electrically or arithmetically, which can be also made a signal of the outgoing light from various kinds of metal structures.

Then, a result measured by the photo detector 15 is compared with calibration data, having created beforehand with having used a solution containing a target substance having known concentration, and is arithmetically operated by a central calculation unit 18, and concentration of the target substance is specified.

Then, measurement results, such as concentration, are displayed on a display unit 19. Here, the calibration data means simultaneous equations, having created beforehand with having used a target substance having known concentration, or a function fn(Xn) which forms the simultaneous equations.

In addition, in the case of creating calibration data, when difference arises by a plurality of target substances performing an interaction in calibration data between the case where they exist in a solution as single components and the case that they coexist, it is necessary to acquire calibration data in consideration of a coexisting substance. That is, the calibration data obtained by measuring signals of respective target substances in a situation that a plurality of target substances exists are acquired. In addition, when target substances do not perform an interaction, each calibration data in a situation that only a target substance exists in a solution as a single component may be created.

A signal obtained from a detecting element which includes a metal structure belonging to a certain arbitrary kind a becomes linear coupling of respective signals from a plurality of target substances, and is expressed in general formula (1).

$$f1(X1)+f2(X2)+f3(X3)\ldots+fn(Xn)=A \quad (1)$$

where fn(Xn): function expressing a concentration responsiveness at the time of concentration of an n-th target substance being Xn in a detecting element which includes a metal structure belonging to a certain kind $\alpha$ Xn: concentration of n-th target substance A: signal obtained from detecting element which includes metal structure belonging to certain kind $\alpha$.

In addition, a signal obtained from a metal structure belonging to another kind $\beta$ is expressed in general formula (2).

$$g1(X1)+g2(X2)+g3(X3)+\ldots+gn(Xn)=B \quad (2)$$

where gn(Xn): function expressing a concentration responsiveness at the time of concentration of an n-th target substance being Xn in a detecting element which includes a metal structure belonging to a certain kind $\beta$ Xn: concentration of n-th target substance B: signal obtained from detecting element which includes metal structure belonging to certain kind $\beta$.

The above-described respective equations in specific elements can be derived by creation of calibration data mentioned above, or by integrating the formulas of calibration data.

Here, when n kinds of target substances exist in a sample, the number of kinds of metal structures is made n or more on a surface of a base material (in other words, n or more kinds of metal structures are provided on the surface of the base material). Thereby, n or more formulas (formulas corresponding to respective kinds of metal structures), such as general formulas (1) and (2), whose solutions are concentrations of n target substances can be obtained. Concentration of the n-th target substance can be specified by solving the simultaneous equations which are constructed of these formulas.

Hence, it is necessary to make the number of kinds of metal structures, whose shapes are different and which are formed on the base material, the number equal to or more than the kinds of target substances which are measuring objects. In addition, although it is preferable to measure signals, obtained from metal structures which belong to different kinds, by separate detecting units, signals which are obtained from metal structures belonging to various kinds, and which are divided clearly can be measured without separating detecting units.

Such an example is a case that peaks are clearly divided on the same spectrum, the same intensity distribution, or the like. The case that peaks are divided clearly is a case that wavelengths are separated to such an extent that a plurality of peaks (local maximum or local minimum) does not affect analysis accuracy. As such an example, a case that a distance between peaks is larger than a half band width of any peak, or the like is cited.

Here, when performing measurement with separating detecting units, it is preferable to divide a region for every kind of metal structure, and to be arranged on a base material.

If necessary, a phosphate buffer and the like may have been introduced from the inlet 5 as cleaning fluid before measurement, and the reaction well 7 may be washed. Here, although a method in the case of measuring a spectral change after a fixed time statically is described, a spectral change can be also measured in real-time. In that case, a time rate of change and the like can be acquired as new information. The above-mentioned operations are input from an input unit 20, a program having been recorded beforehand in an HDD 21 is loaded into RAM 22, and the operations are executed.

Second Embodiment

Next, a second embodiment of the present invention will be described.

In the first embodiment, light is made incident into a detecting element which has two or more kinds of metal structures, and detection signals are obtained. Then, concentrations of target substances are detected by classifying the obtained detection signals into respective kinds of metal structures, and integrating and analyzing them. On the other hand, in this embodiment, concentration of each of a plurality of target substances is detected by acquiring a peak shift amount of a resonance peak in each of the plurality of optical resonance modes, resulting from structure of a metal structure in single structure, as a detection signal, and integrating and analyzing them. As acquisition methods of specific detection signals, a method of calculating analytically the peak shift amounts of the plurality of resonance peaks respectively, and a method of calculating a peak shift amount by making resonance, generated by structure which a metal structure has, selectively resonate by linearly polarized light are cited. In addition, in the present invention, an "optical resonance mode which a metal structure has" means what has characteristically large intensity among vibrating conditions which exist in structure of the metal structure.

In this embodiment, those except that a detecting element, an incident light, and a fractionation method of detection signals are different are the same as those of the first embodiment.

(Incident Light)

Figure 21A:
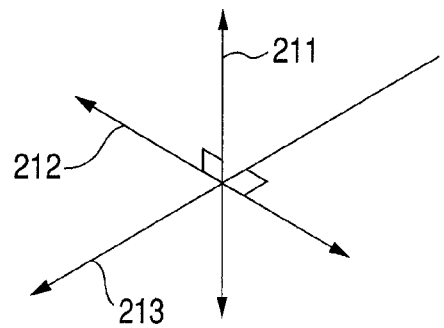
FIGS. 21A, 21B and 21C are schematic diagrams illustrating vibrating directions of an electric field in a second embodiment.
Figure 21B:
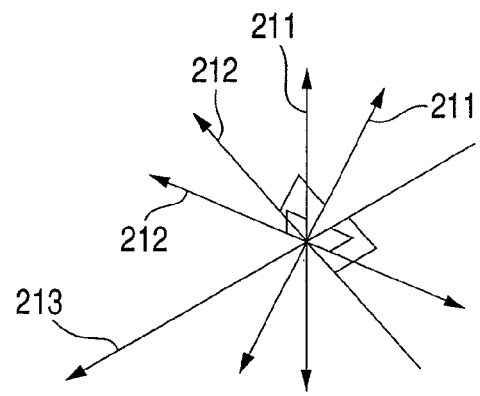
Figure 21C:
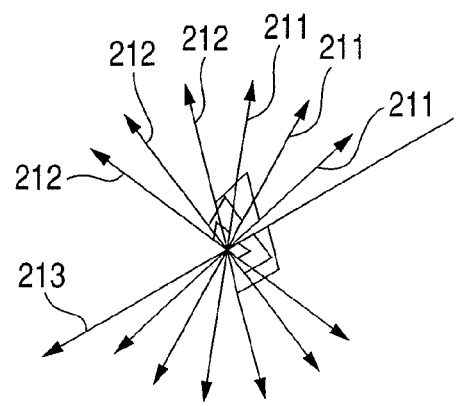

In this embodiment, incident light has a broad band of wavelength sufficient for detecting a peak of a resonance wavelength. In addition, in the case of making a plurality of optical resonance modes resonate at the same time, unpolarized light is selected as incident light, and in the case of making a specific optical resonance mode resonate selectively, linearly polarized light corresponding to each optical resonance mode is made to be incident. In addition, as illustrated in FIG. 21A, light that a vibrating direction 211 of an electric field of light vibrates only in one specific direction is the linearly polarized light. In addition, as illustrated in FIG. 21C, light that a vibrating direction 211 of an electric field vibrates in all the directions in a plane perpendicular to a traveling direction of light is unpolarized light. In FIGS. 21A, 21B and 21C, numeral 212 denotes a vibrating direction of a magnetic field, and numeral 213 denotes a direction of light.

(Detecting Element)

A detecting element of this embodiment is different in a shape of a metal structure from that of the first embodiment to have a plurality of optical resonance modes.

The metal structure in this embodiment has a plurality of optical resonance modes resulting from a geometric feature of structure. Such a metal structure has a shape having anisotropy in projection at the time of light being radiated on the metal structure from a light source in arrangement of performing detection. Here, the shape having anisotropy means a shape which does not become the same shape when it is rotated at an arbitrary angles of 90 degrees or less with a normal line to the above-described projection as an axis.

A rectangle, an ellipse, and the like are cited as such examples. An optical resonance mode at an end of the metal structure is strong in comparison with an optical resonance mode in other portions. Hence, when the projection has a rectangular shape, strength in an optical resonance mode in a long side direction and an optical resonance mode in a short side direction become strong in comparison with those of other resonance modes. When characteristic difference (difference of size of an electric field which oozes out around the metal structure between resonance modes) between resonance modes arises, since effectual detection distances are different, as a result, difference between target substances can be regarded as an optical response for every optical resonance mode.

On the other hand, examples of the shape not having anisotropy are shapes of a regular polygon, circle, and the like. When a projective shape is a shape of a regular polygon or a circle, since difference between line segment lengths (a long side and a short side in a rectangle) of an end is small although a metal structure having such a shape has a plurality of optical resonance modes, characteristic difference between resonance modes (difference of size of an electric field which oozes out around the metal structure between resonance modes) is hardly generated. Hence, when it is a shape which does not have anisotropy, it becomes hard to catch it as an optical response for every optical resonance mode.

In addition, in the above description, although an effect by the shape anisotropy of one metal structure is illustrated, anisotropy of an array direction of metal structures can also achieve the same effect.

(Detecting Method)

Figure 17A:
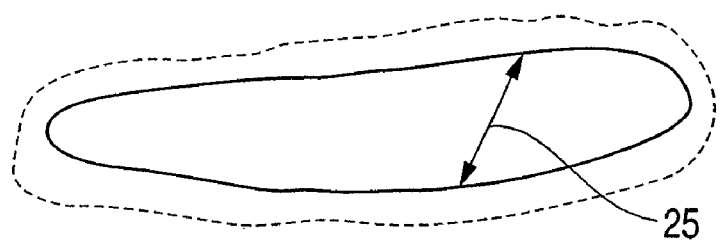
FIGS. 17A and 17B are schematic diagrams illustrating concept of a target substance detecting method in a second embodiment.
Figure 17B:
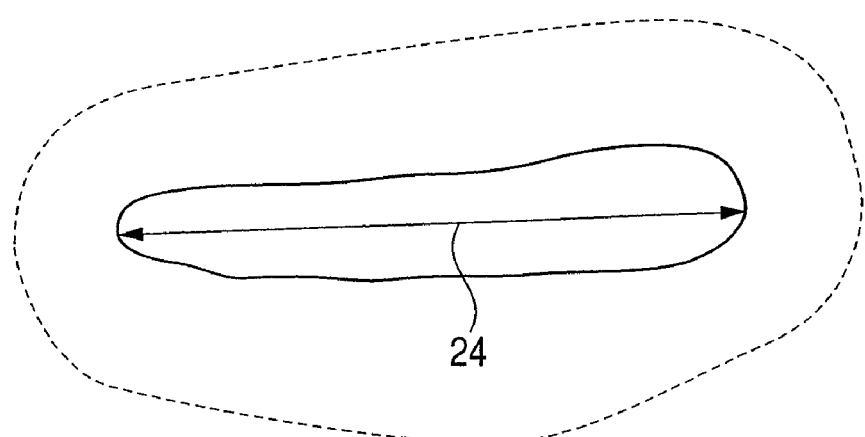

By making the above-described incident light be incident into the above-described metal structure, similarly to the first embodiment, two of localized surface plasmon resonance whose detection sensitivities are different can be generated (FIGS. 17A and 17B). In FIGS. 17A and 17B, in plasmon resonances exist.

Here, first, an acquisition method of a detection signal at the time of using unpolarized light as incident light will be described.

The unpolarized light is made to be incident into a metal structure as incident light, and outgoing light which is emitted from the metal structure by means of transmission, reflection, or scattering is received. When receiving light of the outgoing light, a spectrum apparatus which can acquire intensity for every wavelength of light is used. The intensity for every wavelength of this received light can be obtained as a response characteristic (response spectrum) to incident light. At this time, it is suitable to acquire the response characteristic as relative values on the basis of incident light quantity. In addition, the incident light quantity being a reference can be also acquired as light which is transmitted, reflected, or scattered by a portion having no element.

The acquired response spectrum has a plurality of spectral peaks resulting from a plurality of optical resonance modes. Here, when a plurality of spectral peaks are specified, it is preferable to specify a spectral peak by cutting a spectrum near a local maximum and a local minimum in a fixed wavelength range, and performing fitting with a function suitable to a shape of the spectral peak within the wavelength range. In addition, digital data of each peak wavelength or peak intensity of the plurality of spectral peaks is acquired. Difference between values in a peak wavelength or peak intensity in each of these spectral peaks before and after sample contact is made a detection signal. In addition, as functions suitable for fitting at the time of specifying a spectral peak, there are a Gauss function, a Lorenz function, and a multi-order function, but they are not limited to these.

In addition, an acquisition method of a detection signal at the time of using linearly polarized light as incident light into a metal structure will be described. When linearly polarized light is made to be incident, light which has the same vibrational direction of electric field corresponding to an optical resonance mode of an end of a metal structure is made incident light. Then, a spectrum of outgoing light from a target substance detecting element is acquired by the same method as that in the case that the unpolarized light mentioned above is made to be incident. Spectral peaks derived from the plurality of optical resonance modes resulting from a shape of the metal structure is contained in the spectrum of the outgoing light. Hence, each spectral peak is specified by fitting from the obtained spectrum, similarly to the case that the unpolarized light is radiated. Then, let the difference between the values in the obtained each spectral peak before and after the sample contact be a detection signal.

Thus, by obtaining the plurality of detection signals, similarly to the first embodiment, simultaneous equations with several unknowns (in this example, simultaneous equations with two unknowns) at the time of making two or more kinds of target substances captured can be created. Respective amounts or concentrations of the target substances, which are two or more kinds of target substances having the same recognition site, can be found by solving these simultaneous equations. In addition, several different polarized lights which have different vibrational directions can be used as incident lights to obtain the spectrum of the outgoing light from the corresponding optical resonance mode.

EXAMPLES

The present invention will be further specifically described with examples below. In addition, the present invention is not limited to the following examples.

Reference Example 1

Figure 11:
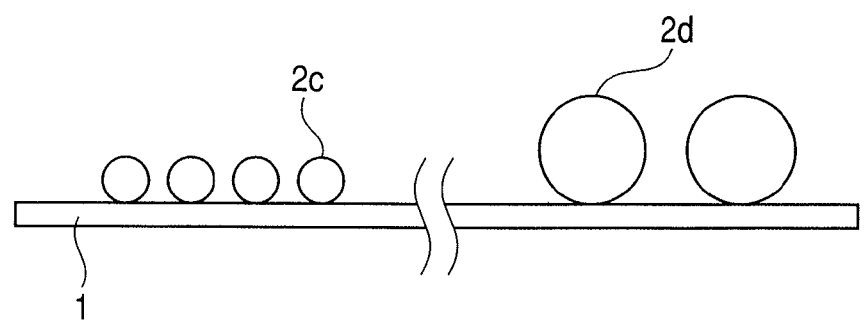
FIG. 11 is a structural example of a first reference example.
Figure 12:
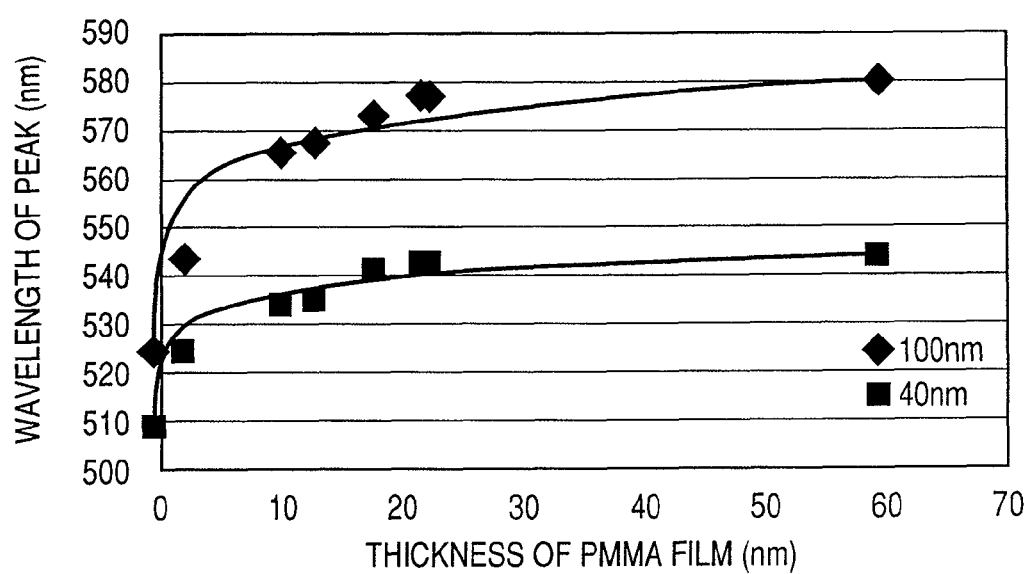
FIG. 12 is a graph where the thickness of a PMMA film, which is produced on a surface of a metal structure in the first reference example, is compared with the wavelength of a peak of plasmon resonance.

An outline of structure of a detecting element used in this example is illustrated in FIG. 11. In golden colloids with two kinds of sizes, 2c was 40 nm in diameter, and 2d was 100 nm (made by BBI in the U.K.) in diameter. As a substrate, a quartz glass substrate (made by Shin-Etsu Chemical Co., Ltd.) on which surface modification was performed with KBM903 was used, the above-described gold colloidal solution was immersed in a detecting unit in one whole day and night, and immobilization was performed. Next, instead of a target substance capturing body, as a model system, a polymethylmethacrylate resin (PMMA) was formed as a film by a spin coating method as a dielectric near fine grains, and PMMA film thickness dependability of a peak wavelength by localized surface plasmon resonance was confirmed (FIG. 12). In addition, the PMMA resin was dissolved in anisole and was used.

From FIG. 12, it was turned out that responsiveness decreases as it separated from a metal surface, and that a change of the responsiveness changed with an element shape. In addition, it was turned out that a case of using a golden colloid element with a large diameter was better in spectral shift quantity, that is, sensitivity.

Example 1

Figure 13A:
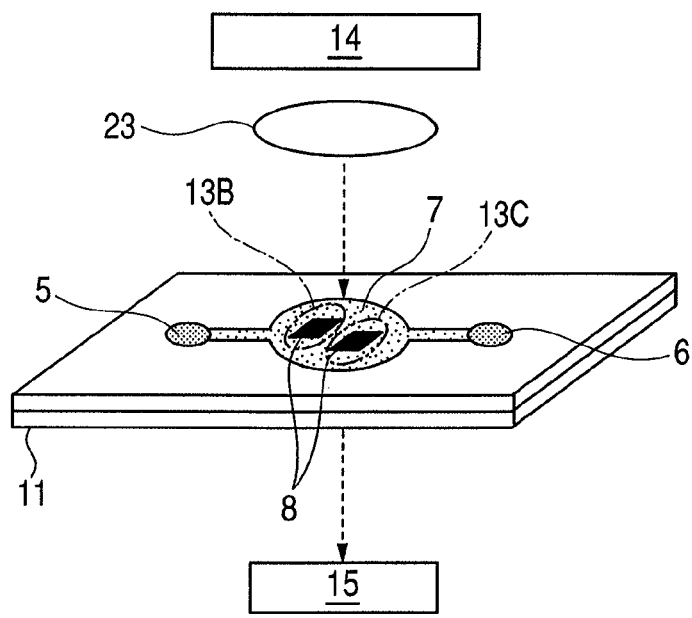
FIGS. 13A, 13B and 13C are schematic diagrams of a target substance detecting apparatus of the first reference example.
Figure 13B:
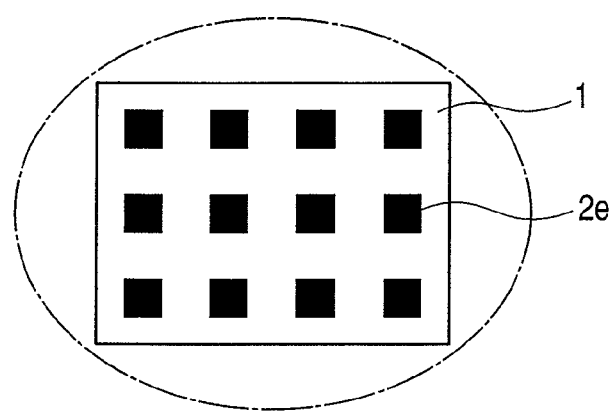
Figure 13C:
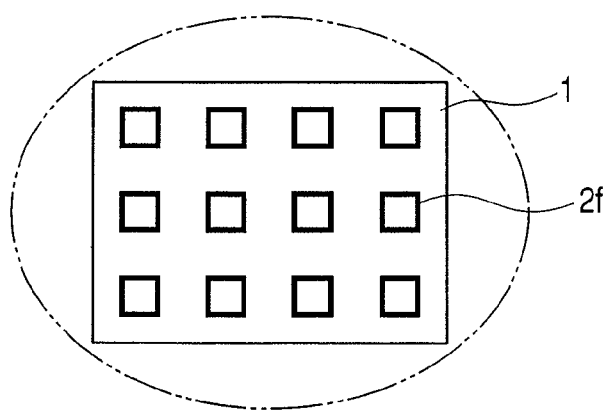
Figure 14A:
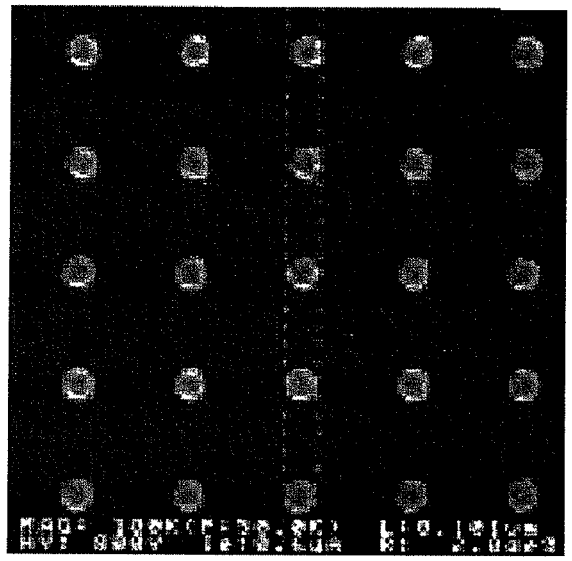
FIGS. 14A and 14B illustrate examples of a SEM image of the target substance detecting element of the first example.
Figure 14B:
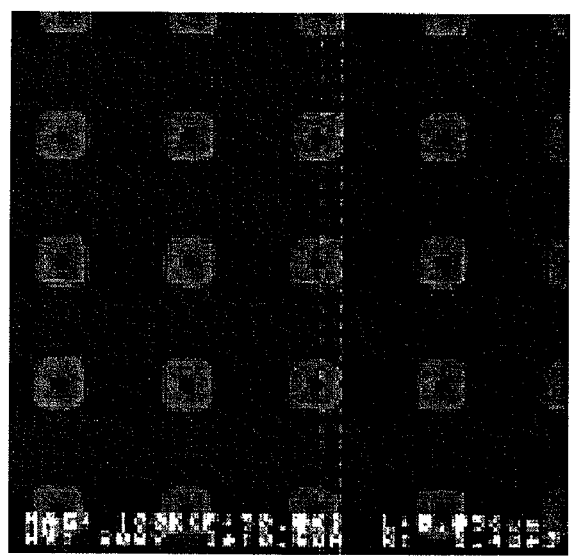

An outline of structure of a detecting apparatus used in this example is illustrated in FIGS. 13A, 13B and 13C. A golden thin film with 20 nm of film thickness was formed on a base material 1 which was a 625 µm-thick quartz plate. Patterning of square metal structures 2e was given to this golden thin film using an electron beam lithography system. At this time, respective metal structures were arranged in an array with a 250 nm space being kept, and were arranged in a 3 mm×3 mm region on the base material. In addition, ring metal structures 2f whose kinds were different from that of the above-described metal structures were produced on another base material 1 by the same method. Scanning electron microscope (SEM) images of the base materials which have two kinds of metal structures, being produced, are illustrated in FIGS. 14A and 14B. It was confirmed that a two-dimensional external form of the metal structure had square shapes with a size of 100 nm×100 nm (FIG. 14A), and 200 nm×200 nm (FIG. 14B) from the SEM images. In addition, the structure illustrated in FIG. 14B had ring structure, and belt width of a ring was 70 nm. Furthermore, the shape may be roundish depending on a height of resolution.

An absorption spectrum of the metal structure in this example has peak wavelengths near 700 nm and near 900 nm in deionized water.

Next, a detecting method using a base material which has these metal structures on a surface will be described.

The base material which has these metal structures on a surface, and the PDMS substrate 11 which has the inlet 5, outlet 6, and reaction well 7 are stuck together.

Then, in order to give capturing bodies to surfaces of the metal structures, anti-ADDL (Amyloid β-derived diffusible ligands) antibodies which are capturing bodies of the target substance ADDL used in this example are fixed to the golden structure surfaces. ADDL is a marker considered to relate to Alzheimer's disease, and a sick degree of seriousness becomes apparent with a size of a subunit. The above-mentioned structure surfaces are modified by dropping an ethanol solution of 11-Mercaptoundecanoic acid, which has a thiol group having high affinity with the gold which is a material of the metal structures of this example, on two-kinds of elements respectively with a spotter or the like. Thereby, carboxyl groups are solidified on the structure surfaces. In the state of immobilizing the carboxyl groups, an N-Hydroxysulfosuccinimide (made by DOJINDO LABORATORIES) aqueous solution, and a 1-Ethyl-3-[3-dimethylamino]propyl]carbodiimide hydrochloride (made by DOJINDO LABORATORIES) aqueous solution are similarly dropped in a reaction region with a spotter to make the carboxyl groups into succinimide groups. Furthermore, by binding streptavidin to the succinimide groups, the structure surfaces are modified with streptavidin. Biotinized anti-ADDL antibodies are made fixed to these structures.

Thereby, two kinds of detecting elements which have anti-ADDL antibodies on surfaces can be produced.

Next, ADDL concentrations of two kinds of molecular weights specifically contained in a sample can be measured by the following operations.

(1) A sample which contains ADDL which is a target is introduced into the manufactured element from the inlet 5 for ADDL to be made to be captured by the capturing bodies which the metal structures have.

(2) The sample is discharged, and a phosphate buffer is introduced from the inlet 5 for an interior of the reaction well 7 to be washed.

(3) Finally, after a phosphate buffer is filled, an absorption spectrum of the gold structures is measured by radiating light.

Figure 15:
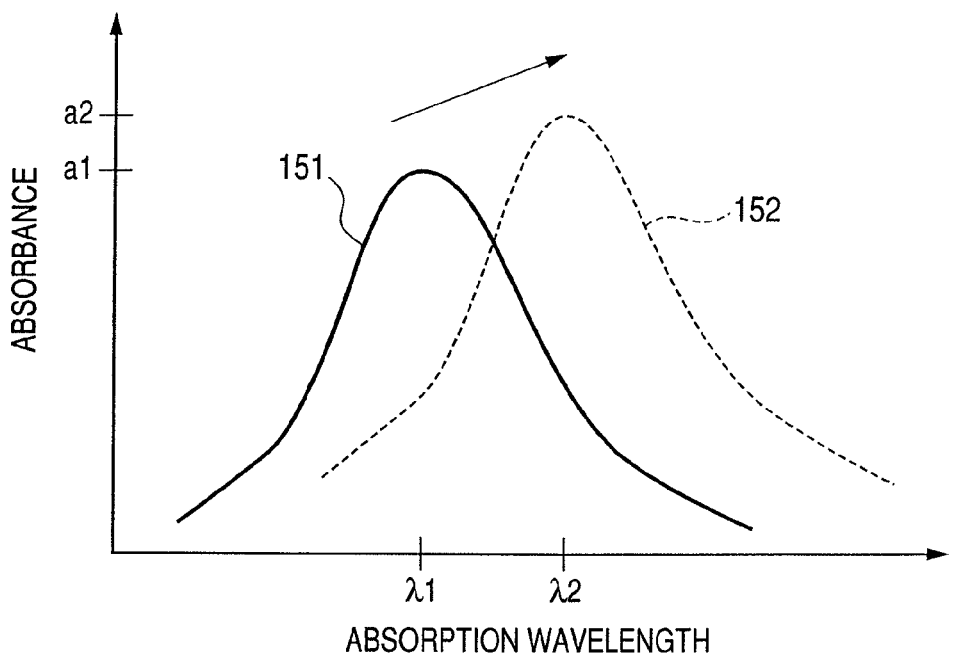
FIG. 15 is a schematic diagram illustrating a change of a detection spectrum (absorption spectrum) of a first example.

A schematic diagram illustrating an example of a change of an absorption spectrum 151 before a reaction and an absorption spectrum 152 after a reaction is illustrated in FIG. 15. When comparing pre-reaction and post-reaction, the absorption spectrum shifts because a target substance bonds with a detecting element surface by a specific antigen-antibody reaction, and a degree of absorbance of a peak is shifted from a1 to a2, and an absorption wavelength of a peak is shifted to $\lambda 2$ from $\lambda 1$. Correlation between a shift amount of peak intensity or peak wavelength of an absorption spectrum in each detecting element, and ADDL concentration can be obtained beforehand by an ADDL control solution whose molecular weights and concentrations are known. Hence, concentrations of the target substances ADDL with two kinds of sizes which were unknown concentrations can be found respectively by solving the following simultaneous equations.

Change of peak shift amount or peak intensity of 200 nm square element: $aX+bY$

Change of peak shift amount or peak intensity of 100 nm square element: $cX+dY$ where a, b, c, d: coefficients determined from ADDL with known concentrations X, Y: unknown ADDL concentrations of two kinds of sizes.

Example 2

Figure 18A:
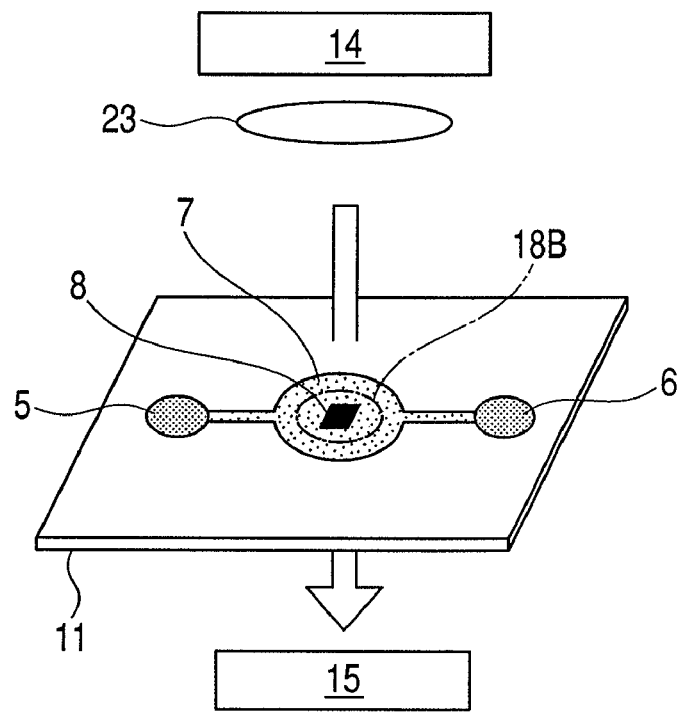
FIGS. 18A and 18B are schematic diagrams of a target substance detecting apparatus of a second example.
Figure 18B:
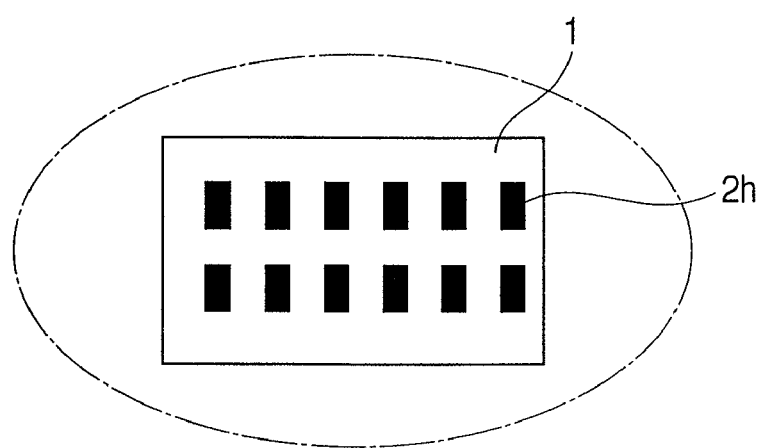
Figure 19:
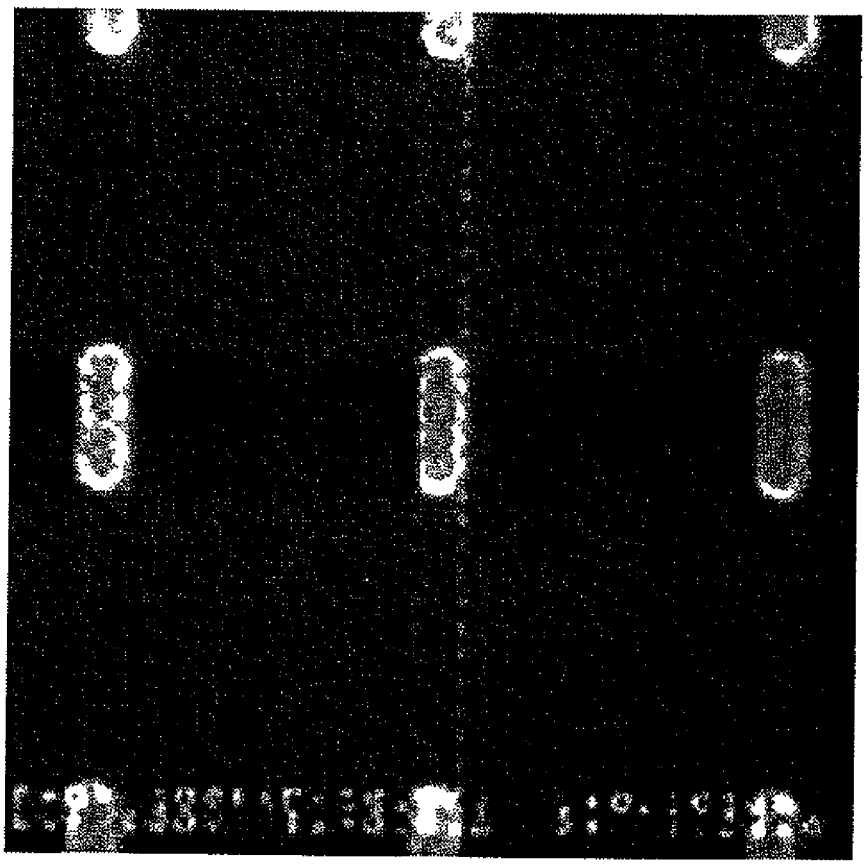
FIG. 19 illustrates an example of a SEM image of a target substance detecting element of the second example.

An outline of structure of a detecting apparatus used in this example is illustrated in FIGS. 18A and 18B. A golden thin film with 20 nm of film thickness was formed on a base material 1 which was a 625 μm-thick quartz plate. Patterning of golden metal structures 2h being rectangular was given to this golden thin film using an electron beam lithography system. At this time, respective metal structures were arranged in an array with a 600 nm space being kept, and were arranged in a 3 mm×3 mm region on the base material. In addition, the light source unit 14 is constructed of including a tungsten lamp, and the photo detector 15 is constructed of including a spectrophotometer. A scanning electron microscope (SEM) image of the base material which has the golden structure, being produced, is illustrated in FIG. 19. It was confirmed that a two-dimensional external form of the golden structure had a rectangular shape with a size of 300 nm×100 nm from the SEM image. In addition, the shape may be roundish depending on a height of resolution. As for the absorption spectrum of the metal structure in this example, when it exists in deionized water and broadband unpolarized light is radiated, characteristic absorption peaks are observed near 650 nm and near 1400 nm.

Next, a detecting method using a base material which has these metal structures on a surface will be described.

The base material which has these metal structures on a surface, and the PDMS substrate 11 which has the inlet 5, outlet 6, and reaction well 7 are stuck together.

Then, in order to give capturing bodies to surfaces of the metal structures, anti-ADDL (Amyloid β-derived diffusible ligands) antibodies which are capturing bodies of the target substance ADDL used in this example are fixed to the golden structure surfaces. ADDL is a marker considered to relate to Alzheimer's disease, and a sick degree of seriousness becomes apparent with a size of a subunit. The above-mentioned structure surfaces are modified by dropping an ethanol solution of 11-Mercaptoundecanoic acid, which has a thiol group having high affinity with the gold which is a material of the metal structures of this example, on the element respectively with a spotter or the like. Thereby, carboxyl groups are solidified on the structure surfaces. In the state of immobilizing the carboxyl groups, an N-Hydroxysulfosuccinimide (made by DOJINDO LABORATORIES) aqueous solution, and a 1-Ethyl-3-[3-dimethylamino]propyl]carbodiimide hydrochloride (made by DOJINDO LABORATORIES) aqueous solution are similarly dropped in a reaction region with a spotter to make the carboxyl groups into succinimide groups. Furthermore, by binding streptavidin to the succinimide groups, the structure surfaces are modified with streptavidin. Biotinized anti-ADDL antibodies are made fixed to these structures.

Thereby, the detecting element which has anti-ADDL antibodies on the surface can be produced.

Subsequently, ADDL concentrations of two kinds of molecular weights specifically contained in a sample can be measured by the following operations.

(1) A sample which contains ADDL which is a target is introduced into the manufactured element from the inlet 5 for ADDL to be made to be captured by the capturing bodies which the metal structures have.

(2) The sample is discharged, and a phosphate buffer is introduced from the inlet 5 for an interior of the reaction well 7 to be washed.

(3) Finally, after a phosphate buffer is filled, an absorption spectrum of the gold structures is measured by radiating broadband unpolarized light.

Figure 20:
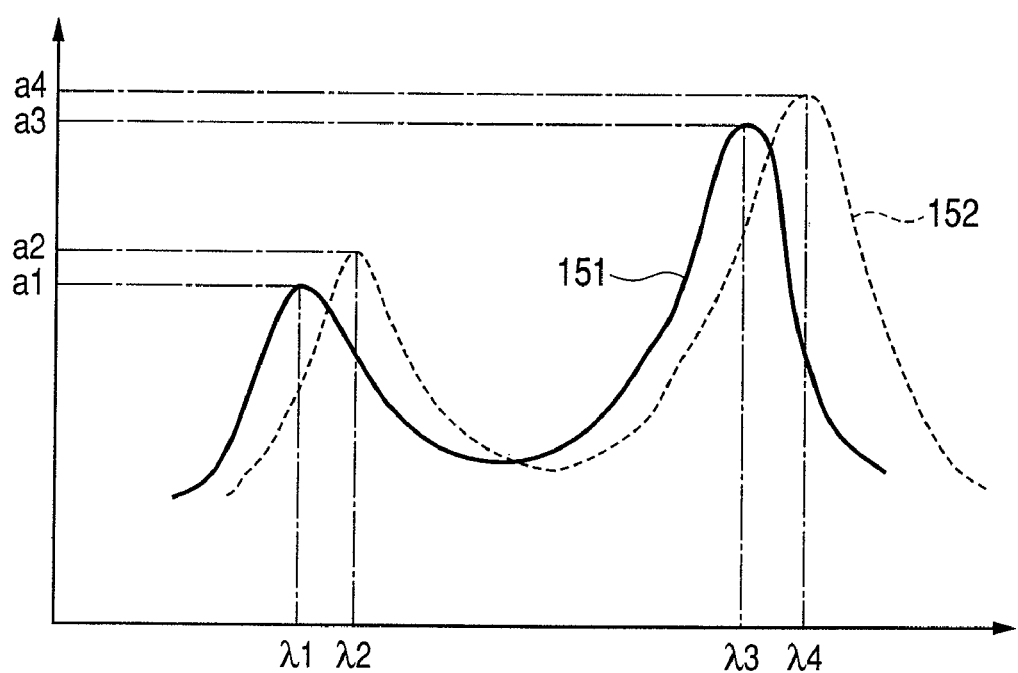
FIG. 20 is a schematic diagram illustrating a change of a detection spectrum (absorption spectrum) of the second example.

A schematic diagram illustrating an example of a change of an absorption spectrum 151 before a reaction and an absorption spectrum 152 after a reaction is illustrated in FIG. 20. When comparing pre-reaction and post-reaction, the absorption spectrum shifts because a target substance bonds with a detecting element surface by a specific antigen-antibody reaction. That is, amplitude of absorbance of a spectral peak corresponding to an optical resonance mode corresponding to a shorter end 25 among ends which the metal structure 2 illustrated in FIG. 22 has changes from a1 to a2, and the absorption wavelength changes from λ1 to λ2, and a degree of absorbance of a spectral peak corresponding to an optical resonance mode corresponding to a longer end 24 changes from a3 to a4, and the absorption wavelength changes from λ3 to λ4. In addition, FIG. 22 is a diagram of viewing the metal structure, which is a rectangular solid, from a direction of radiating light.

In the example mentioned above, although the spectrum near the peak in the specific resonance mode is selectively acquired from the full absorption spectrum of broadband light, a peak in a specific resonance mode can be also acquired by controlling polarization of incident broadband light. Such a case is described below.

Figure 22:
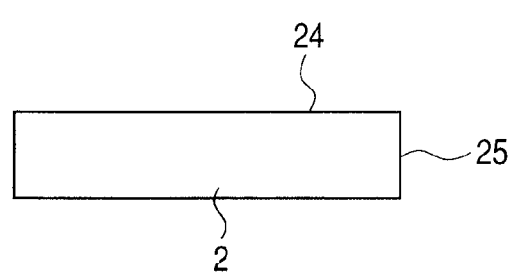
FIG. 22 is a schematic diagram illustrating a change of an absorption spectrum of a specific resonance mode in a second example.

When linearly polarized light which has an electric field which vibrates in a direction parallel to the end 25 in FIG. 22 is made incident light, only an absorption spectrum resulting from an optical resonance mode corresponding to the end 25 can be acquired. In addition, similarly, when linearly polarized light which has an electric field which vibrates in a direction parallel to the end 24 in FIG. 22 is made incident light, only an absorption spectrum resulting from an optical resonance mode corresponding to the end 24 can be acquired.

Figure 23A:
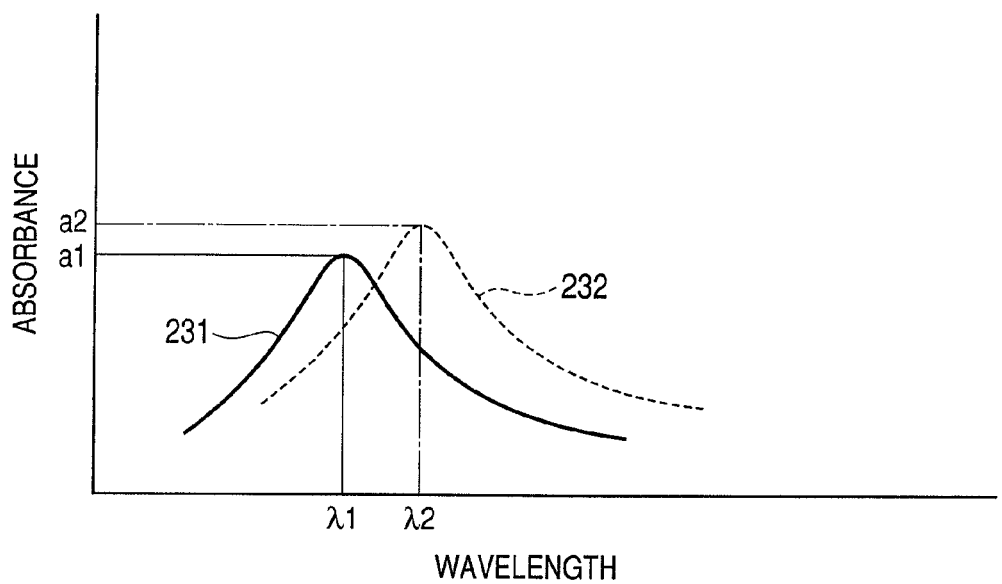
FIGS. 23A and 23B are schematic diagrams illustrating changes of a detection spectrum (absorption spectrum) of the second example.
Figure 23B:
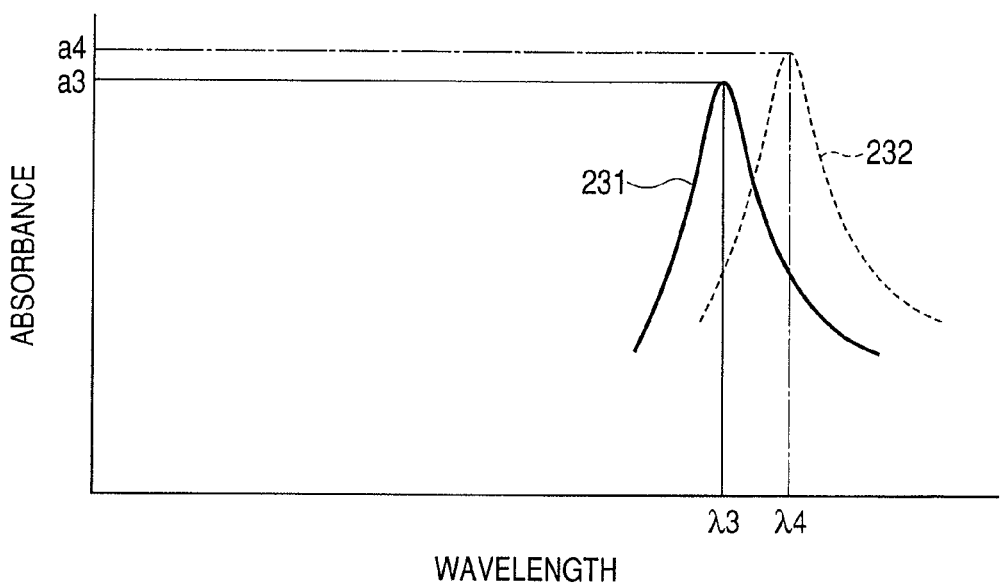

Changes of the absorption spectrum 231 to 232 in these cases are illustrated in FIGS. 23A and 23B. When linearly polarized light which has an electric field which vibrates in a direction parallel to the end 25 is made incident light, as for the absorption spectrum resulting from the optical resonance mode corresponding to the end 25, the wavelength of the spectral peak changes from λ1 to λ2, and a degree of absorbance of the spectral peak changes from a1 to a2. In addition, when linearly polarized light which has an electric field which vibrates in a direction parallel to the end 24 in FIG. 22 is made incident light, as for the absorption spectrum resulting from the optical resonance mode corresponding to the end 24, the wavelength of the spectral peak changes from λ3 to λ4, and a degree of absorbance of the spectral peak changes from a3 to a4.

With any method, variations of a peak of an absorption spectrum corresponding to the end 24 and end 25 in the metal structure of FIG. 22 can be obtained.

Correlation between a shift amount of peak intensity or peak wavelength of an absorption spectrum in each detecting element, and ADDL concentration can be obtained beforehand by an ADDL control solution whose molecular weights and concentrations are known. Hence, as mentioned above, concentrations of the target substances ADDL with two kinds of sizes which were unknown concentrations can be found respectively by acquiring the shift amount of the peak wavelength or peak intensity of the absorption spectrum and solving the following simultaneous equations.

Shift amount of spectral peak or peak intensity change generated by electric field in vibrating direction of A: $aX+bY$.

Peak shift amount or peak intensity change generated by electric field in vibrating direction of B: $cX+dY$ where a, b, c, d: coefficients determined from ADDL with known concentrations X, Y: unknown ADDL concentrations of two kinds of sizes.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2006-133848, filed May 12, 2006, and No. 2007-125241, filed May 10, 2007, which are hereby incorporated by reference herein in their entirety.

The invention claimed is:

1. A target substance detecting apparatus using localized surface plasmon resonance, which detects kinds of target substances which have the same recognition site recognized by a specific capturing body but whose kinds are different mutually, comprising a target substance detecting element, a reaction mechanism for contacting a sample containing a target substance with the target substance detecting element, a light source for irradiating the target substance detecting element with light, a detecting unit for detecting a detection signal from the target substance detecting element, and an analyzing unit for analyzing the detection signal to determine the target substance, the target substance detecting element comprising a base material, two or more kinds of metal structures which are mutually different in shape, material or size and which give rise to localized surface plasmon resonance by receiving the light, provided on a surface of the base material, and a target capturing unit provided on each surface of the metal structures;

the detecting unit acquiring a spectrum of outgoing light from the target substance detecting element contacted with the sample, classifying the acquired spectrum according to kind of the metal structures to determine spectral peaks, and detecting a change of the spectral peak of each kind of the metal structures from the state before the contact with the sample to the state after the contact as the detection signal; and the analyzing unit integrating and analyzing the detected detection signals to calculate the concentration of each kind of the target substances.

2. The target substance detecting apparatus according to claim 1, wherein the number of kinds of the metal structures are equal to or more than the number of kinds of the target substances.

3. The target substance detecting apparatus according to claim 1, wherein the analyzing unit uses simultaneous equations with several unknowns to calculate the concentration.

4. The target substance detecting apparatus according to claim 1, wherein the analyzing unit calculates the concentration from data for a calibration which has been obtained beforehand through solutions of the target substance in known concentrations.

* * * * *